United States Patent [19]
Voorhees et al.

[11] Patent Number: 6,017,960
[45] Date of Patent: *Jan. 25, 2000

[54] METHOD OF TREATING POST-INFLAMMATORY HYPERPIGMENTATION IN BLACK SKIN WITH A RETINOID, AND METHOD OF LIGHTENING BLACK SKIN WITH A RETINOID

[75] Inventors: John J. Voorhees; Charles N. Ellis, both of Ann Arbor, Mich.; Christopher E. M. Griffiths, Manchester, United Kingdom

[73] Assignee: Regents of the University of Michigan, Ann Arbor, Mich.

[ * ] Notice: This patent is subject to a terminal disclaimer.

[21] Appl. No.: 09/076,355

[22] Filed: May 12, 1998

Related U.S. Application Data

[63] Continuation-in-part of application No. 07/861,133, Mar. 31, 1992, Pat. No. 5,750,570.

[51] Int. Cl.[7] .................................................... A61K 31/19
[52] U.S. Cl. .............................. 514/557; 514/725; 424/59
[58] Field of Search .................................. 514/557, 725; 424/59

[56] References Cited

U.S. PATENT DOCUMENTS

5,750,570   5/1998   Voorhees et al. ..................... 514/557

*Primary Examiner*—Jose' G. Dees
*Assistant Examiner*—Michael A. Williamson
*Attorney, Agent, or Firm*—Hopgood, Calimafde Kalil & Judlowe LLP

[57] ABSTRACT

Treatment of post-inflammatory hyperpigmentation (PIH) in black and asian skin is accelerated from natural healing by use of a composition comprising a retinoid and/or an inhibitor of cytochrome P-450 enzyme-mediated degradation of retinoids, the composition does not require a conventional depigmenting or bleaching agent (such as a hydroquinone) as is typically used. Healing of PIH lesions is accelerated about three to five times from normal healing. Additionally, these compositions are useful separately for lightening black or asian skin.

23 Claims, 3 Drawing Sheets

METHOD OF TREATING POST-INFLAMMATORY HYPERPIGMENTATION IN BLACK SKIN WITH A RETINOID, AND METHOD OF LIGHTENING BLACK SKIN WITH A RETINOID

This application is a continuation-in-part of application Ser. No. 07/861,133, filed Mar. 31, 1992, now U.S. Pat. No. 5,750,570, the disclosure of which is incorporated herein by reference.

BACKGROUND

1. Technical Field

The present method relates to a method of treating hyperpigmentation in black skin with retinoic acid and a method of lightening black skin with retinoic acid.

2. Background Art

Post inflammatory hyperpigmentation (PIH) presents as irregular, darkly-pigmented spots occurring after inflammation due to an injury to the skin from an insult such as acne, folliculitis, eczema, or shaving. PIH resolves slowly but may persist for months. Black (e.g., Negroid) subjects of all ages are commonly afflicted with PIH, and the consequent disfigurement may necessitate medical attention (J. A. Kenney, Jr., et al., *Clinics in Dermatology*, 1989; 7:1–10; P. E. Grimes et al., *Dermatologic Clinics*, 1988; 6:271–81; and C. J. McDonald et al., *Progress in Dermatology*, 1979, 4:15–20). Although the biology of skin pigmentation is relatively well-understood, therapy for PIH is unsatisfactory and currently available therapies, such as the use of hydroquinones as bleaching agents, can result in unsightly depigmentation, irritant dermatitis, and ochronosis (C. J. McDonald, *Prog. in Dermatol.*, 1973; 4:15–20; Kligman A. M. et al., *Arch. Dermatol.*, 1975; 111:40–48; G. H. Findlay et al., *Br. J. Dermatol.*, (1975) 93:613–22; and R. A. Hashaw et al., *Arch. Dermatol.*, (1985) 121:105–8). Exemplary of such therapies is one described by Nair et al. (EP-A1-421, 110) in which 4-hydroxyanisole (a hydroquinone derivative) and a retinoid are topically administered to treat hyperpigmentation associated with freckles, senile lentigo, lentigines, melasma, PIH, sunburn, and phototoxic reactions; from the Nair et al. disclosure the retinoid appears to be present because it is disclosed as decreasing the thickness of the stratum corneum and thus possibly facilitating the penetration of topically-administered bleaching agents (though the decrease occurs over time).

In recent studies on the use of topically applied retinoic acid (RA) for the treatment of photodamaged skin, lightening of sun-induced dyspigmentation, i.e., actinic lentigines, has been observed (J. S. Weiss et al., *JAMA*, 259:527–32 (1988); A. M. Kligman et al., *J. Am. Acad. Dermatol.*, 15:836–59 (1986); G. D. Weinstein et al., *Arch. Dennatol.*, 127:659–65 (1991); E. S. Rafal et al., *New Engl. J. Med.*, 326:368–374 (1992); C. N. Ellis et al., *J. Am. Acad. Dennatol.*, 23:629–37 (1990); and E. A. Olsen et al., *J. Am. A cad. Dermatol.*, 26:215–24 (1992)). Sun-induced dyspigmentation is a heterogeneous entity in whites (E. S. Rafal et al., *New Engl. J. Med.*, 326:368–374 (1992)) which may share features of melanin deposition with PIH. RA has not been used previously for PIH because it was thought to cause, rather than ameliorate, hyperpigmentation, and to be poorly tolerated (C. J. McDonald et al., *Prog. in Dermatol.*, 4:15–20 (1992)). Topical RA treatment has also been reported as effective for the treatment of liver spots associated with photodamage (E. S. Rafal et al., *New Engl. J. Med.*, 326:368–74 (1992)).

A need remains in the art for a method of treating post-inflammatory hyperpigmentation. In addition, a method of lightening black skin would also be desirable.

SUMMARY AND OBJECTS OF THE INVENTION

Accordingly, it is one object of the present invention to provide a method for treating hyperpigmentation in black and asian skin. A more particular object of the present invention is to provide a method for treating PIH (post-inflammatory hyperpigmentation) in black skin.

Another object of the invention is to provide a method for lightening black skin.

These and other objects, which will become apparent during the following detailed description, have been achieved by our discovery that retinoids, especially retinoic acid and retinol, are effective for treating post-inflammatory hyperpigmentation in black skin. We have separately discovered that retinoids are useful for lightening black skin. In the appended claims, the term "consisting essentially of" is intended to focus on the use of retinoids as claimed for the particular method of treatment and to exclude hydroquinones and similar and related bleaching or depigmentation compositions.

BRIEF DESCRIPTION OF THE DRAWINGS

A more complete appreciation of the invention and many of the attendant advantages thereof will be readily obtained as the same become better understood by reference to the following detailed description when considered in connection with the accompanying drawings, now briefly described.

FIG. 3 depicts the calorimeter-measured color change of individual PIH lesions and normal skin in response to treatment with 0.1% RA cream (open bars) or a control composition (solid bars). An increase in the reflectance value (L) by calorimeter indicates a lightening in skin color. Values are means ±S.E.M. After 12 weeks of treatment with 0.1% RA cream there was significant lightening of pigmented lesions as compared with treatment with the control ($p=0.05$). This RA-induced lightening continued to 40 weeks ($p=0.05$). Normal skin treated with 0.1% RA cream lightens as compared with the baseline, whereas normal skin treated with the control vehicle darkened over the 40 week treatment period ($p=0.0001$); this lightening took place slowly with no statistically significant difference between RA and the control composition at the end of the 12 week period.

DETAILED DESCRIPTION OF SPECIFIC EMBODIMENTS

Thus, in a first embodiment, the present invention relates to a method of treating hyperpigmentation in black skin with retinoic acid. All trans retinoic acid is a known compound having the formula:

The preparation of retinoic acid is described in U.S. Pat. No. 3,006,939, and by Lakshmanan et al., *Biochem. J.*, vol. 90, p. 569 (1964); the structure was confirmed by x-ray crystallography by Stan et al. (Acto Cryst., vol. 16, p. 62 (1963)). The properties of retinoic acid are reviewed by Dowling et al. (*Vitam. Horm.*, vol. 18, p. 515 (1960)). The disclosures of these publications are incorporated herein by reference.

It should be understood that the present methods of treating hyperpigmentation and lightening skin may be applied to other types of non-caucasian skin, such as asian skin, in addition to black skin.

Although the present invention is described with reference to the use of retinoic acid, it should be understood that the present methods of treating hyperpigmentation and lightening skin may be carried out by using one or more retinoids. This class of compounds includes natural and synthetic analogs of vitamin A (retinol), vitamin A aldehyde (retinal), vitamin A acid (retinoic acid (RA), including all-trans, 9-cis, and 13-cis retinoic acid), etretinate, and others as described in EP-A2-0 379367, U.S. Pat. No. 4,887,805, and U.S. Pat. No. 4,888,342, and the dissociating retinoids that are described by Fanjul et al. in Nature (1994) 372:104–110 (the disclosures of which are all incorporated herein by reference). Various synthetic retinoids and compounds having retinoid activity are expected to be useful in this invention, to the extent that they exhibit retinoid activity in vivo, and such are described in various patents assigned on their face to Allergan Inc., such as in the following U.S. Pat. Nos. 5,514,825; 5,698,700; 5,696,162; 5,688,957; 5,677,451; 5,677,323; 5,677,320; 5,675,033; 5,675,024; 5,672,710; 5,688,175; 5,663,367; 5,663,357; 5,663,347; 5,648,514; 5,648,503; 5,618,943; 5,618,931; 5,618,836; 5,605,915; 5,602,130. Still other compounds described as having retinoid activity are described in other U.S. Pat. Nos. 5,648,563; 5,648,385; 5,618,839; 5,559,248; 5,616,712; 5,616,597; 5,602,135; 5,599,819; 5,556,996; 5,534,516; 5,516,904; 5,498,755; 5,470,999; 5,468,879; 5,455,265; 5,451,605; 5,343,173; 5,426,118; 5,414,007; 5,407,937; 5,399,586; 5,399,561; 5,391,753; and the like. The disclosures of all of the foregoing patents and literature references are incorporated herein by reference. While retinol is the preferred compound for topical administration, effective derivatives of retinol that would be expected to be useful for practicing this invention specifically include retinal, retinoic acid (including all-trns, 9-cis, and 13-cis isomers), and derivatives thereof (such as 7,8-didehydroretinoic acid), and others as described by Kligman et al., including cosmetically acceptable salts, esters, reverse esters, and ethers thereof, conjugates thereof, and mixtures thereof Any compound administrable in a non-toxic amount and having retinoic acid activity in vivo is expected to be useful for practicing this invention. In general, any compound that binds to the retinoic acid receptor (RAR) or the retinoid X receptor (RXR) and thus transactivates and/or transrepresses RA-sensitive genes s a retinoid that is likely to function in the present invention. Binding of a compound to RAR or RXR can be determined using well-known techniques (e.g., immunologically by making the test compound using a radioactive element and determining with antibodies whether it has bound to the receptor, or whether it displaces a radioactive RA from its receptor binding site). Another method for determining retinoid activity in vivo is to biopsy a patch area of skin treated with the candidate retinoid compound and determine if CRABP (cytoplasmic retinoic acid binding protein) concentrations are increased, thus indicating that the candidate compound acts as a retinoid in the skin.

In addition to retinoids as a class of compounds useful for this invention, any drug which inhibits the cytochrome P-450 enzymes that metabolize retinoic acid can also be useful in practicing this invention. In the skin, retinoic acid (RA) is metabolized to inactivation by hydroxylation (via RA 4-hydroxylase) to 4-hydroxy-RA, which is then oxidized to 4-oxo-RA by a reaction mediated by a cytochrome P-450-dependent monooxygenase system. (S. Kang et al., "Liarozole Inhibits Human Epidermal Retinoic Acid 4-Hydroxylase Activity and Differentially Augments Human Skin Responses to Retinoic Acid and Retinol In Vivo," *J. Invest. Dermatol.*, 107:183–187 (Aug. 1996); E. A. Duell et al., "Human Skin Levels of Retinoic Acid and Cytochrome P-450-derived 4-Hydroxyretinoic Acid after Topical Application of Retinoic Acid In Vivo Compared to Concentrations Required to Stimulate Retinoic Acid Receptor-mediated Transcription In Vitro," *J. Clin. Invest., Skin Retinoid Levels and Reporter Gene Activity*, 90:1269–1274 (October 1992); E. A. Deull et al., "Retinoic Acid Isomers Applied to Human Skin in Vivo Each Induce a 4-Hydroxylase That Inactivates Only Trans Retinoic Acid," *J. Invest. Dermatol.*, 106:316–320 (February 1996); the disclosures of which are incorporated herein by reference). Accordingly, compounds which interfere with the elimination metabolism of all trans RA, the active metabolite of topically applied retinoids such as 9-cis RA and 13-cis RA, will beneficially increase the amount of RA in the skin. Thus, preventing the degradation of natural (all trans) RA in the skin effectively increases its concentration, and so likely provides the benefits described herein. Compounds dermatologically acceptable and having or likely to have inhibitory effects on the P-450-mediated degradation of retinoids (e.g., RA) include azoles, especially triazoles, including, for example, ketoconazole (U.S. Pat. Nos. 4,144,346 and 4,223,036), fluconazole (U.S. Pat. No. 4,404,216), itraconazole (U.S. Pat. No. 4,267,179), liarozole, irtemazole, and the like; compounds related to these that may also be useful include, for example, diazines such as flucytosine. Still further, analytical methods are available for determining whether a given compound inhibits the degradation of RA by applying the compound and testing for changes in CRABP (cytoplasmic retinoic acid binding protein), which will have increased levels if the natural levels of RA are also increased by the inhibitory effects due to the topical application of the test compound.

In the present method for treating PIH in black skin, the retinoid is preferably administered by applying a composition containing one or more retinoids directly to the portion of the skin to be treated. The composition, exemplary ones of which are described below, is applied in an amount effective for treating PIH; effective amounts or retinoids for this invention are typically in the range of 0.005 to 10 wt. %, preferably 0.5–10%, and more preferably 1–5% of the composition applied. While ingredients for systemic administration are typically dosed in weight percentages based on the weight of the patient (e.g., (unit weight of ingredient)/

(unit weight of patient), such as mg/kg), ingredients administered topically to skin are typically dosed as a weight percentage of the composition applied (e.g., a cream comprising 1% by weight of retinoic acid). Thus, for example, topically administering a 0.25% cream four times a day is equivalent to administering a 1% cream once daily.

The administration of the retinoid to the skin preferably is carried out in a repetitive fashion. For example, it is preferred that the composition be applied from 3 to 7 times per week, especially once each and every day. Especially good results have been obtained when retinoic acid is used and is applied to the skin on a daily basis. It is particularly preferred that the retinoid be applied in the evening, immediately after the skin has been washed and dried.

The repeated topical administration of the retinoid-containing composition is carried out over a period of time effective to ameliorate the post-inflammatory hyperpigmentation. To achieve this end, the treatment typically is carried out for a period of 4 to 40 weeks, although more typically results can be achieved by 20 weeks.

It may be advantageous, when carrying out the treatment over a period of weeks or months, to start the treatment with an initial dosage of 0.05–1%, more preferably 0.1–0.5%, and then gradually increase the dosage to 0.5–10%, more preferably 1–5% as the patient's skin becomes acclimated to the treatment. If the patient develops an irritation due to the retinoid (not uncommon when retinoic acid is used) during treatment, treatment should be discontinued for 1–4 days, although more usually 1–2 days is sufficient, or in aggravated cases until the irritation subsides; use of retinol is less likely to irritate.

As noted above, the retinoid is administered topically and is formulated in a dermatologically suitable composition. The primary requirement with regard to the concentration of the retinoid in the composition is that it be present in an amount sufficient to provide an amount of the retinoid in the skin effective to ameliorate PIH during the course of treatment. Although skin types vary, and an individuals' self-administration of a topical medicament will result in variations in the amount actually administered, the concentration of retinoic acid as a retinoid effective for treating PIH, is usually 0.025 to 0.2 wt. %, more preferably 0.05 to 0.1 wt. %, and most preferably about 0.1 wt. % based an the total weight of the composition. While at present it is not the most preferred route of administration, oral administration of a compound that provides retinoid activity in the skin will likely also be useful for treating hyperpigmentation.

Compositions useful for practicing this invention may take any form which is suitable for topical administration to human skin. Thus, the composition may be in the form of an oil- or petroleum-based composition (e.g., an ointment), a water-based composition (e.g., an emulsion such as a cream, lotion, or gel), and the like. The composition may contain one or more additional ingredients such as water, oil, alcohol (such as ethanol, isopropanol, propanol, or glycol), an emulsifier, an odorant or fragrance, a colorant (dye, pigment), a filler, an exfoliant (abrasive) agent, a humectant, a moisturizer, and the like, and mixtures thereof compatible with each other and with the retinoid. Especially good results have been obtained using 0.1% Retin-AO™ Cream (commercially available product of Ortho Pharmaceutical Corp., Raritan, N.J.).

The present method of treating hyperpigmentation is especially effective for treating PIH in black skin.

In a second embodiment, the present invention relates to a method of lightening black skin with a retinoid such as retinoic acid. Again, the retinoid may be applied directly to the skin in the form of a composition to the skin to be lightened. The same compositions used for the treatment of PIH may be used for the lightening of black skin. In general, the method of lightening black skin may be carried out as described above for the method of treating PIH. However, in the case of lightening black skin, it may be desirable to maintain the treatment for longer periods of time than for treating PIH, e.g., 20 to 40 weeks versus four to 20 weeks.

The efficacy of the retinoid for treating PIH of black skin and for lightening black skin has now been demonstrated by clinical studies. The present data demonstrate the short term tolerability and efficacy of a retinoic acid composition, such as a 0.1 wt. % cream (0.1% RA) for the treatment of hyperpigmentation, in particular PIH, in black skin. Clinically significant lightening of PIH lesions occurred with use of 0.1% RA, and side effects occurred in fewer of these black subjects (53%) than were reported in whites (88%) (J. S. Weiss el al., $JAMA$, 259:527–37 (1988); and E. S. Rafel et al., $New Engl. J. Med.$, 326:368–374 (1992)). Contrary to prior reports (C. J. McDonald et al., $Prog. in Dermatol.$, 4:15–20 (1973)), topically applied 0.1% RA cream did not result in excessive hyperpigmentation or unwanted depigmentation of the skin in any of the patients we have studied.

Topically administered RA has been reported to lighten hyperpigmented lesions, i.e., actinic dyspigmentation and nevi, in Caucasian skin (Weiss et al. (1988), Kligman (1986); Weinstein et al. (1991); Rafal et al. (1992), Ellis et al. (1990), and Olsen et al. (1992), all cited above; L. Edwards et al., $Arch. Dermatol.$, 126:494–9 (1990); and F. L. Meyskens, Jr., et al., $J. Am. Acad. Dermatol.$, 15:822–5 (1986)). In the present study, 22 of 24 patients (92%) in the RA-treated group demonstrated clinically significant improvement after 40 weeks of treatment. However, 17 of 30 patients (51%) on vehicle (control) therapy also demonstrated lightening of PIH lesions at week 40. This is probably due either to subjects' employing a daily skin care regimen that included sunscreen, or more likely to the spontaneous fading of PIH lesions (which fading is known to occur after several months). Nevertheless, it is notable that clinically identifiable lightening occurred earlier in retinoic acid-treated individuals (4 weeks) as compared with vehicle-treated patients (24 weeks). This result is considered to be of practical relevance in that improvement can be expected as early as 4 weeks in some patients (38%).

The results of skin lightening were confirmed using a calorimeter to measure the apparent color of the skin, thus demonstrating significant lightening of designated PIH lesions and normal skin by RA therapy in comparison with vehicle treatment alone. This finding has not been reported previously. Although the underlying mechanism of action is unknown and is not relied upon for patentability, Orlow has reported that retinoic acid will inhibit tyrosinase which has already been reduced to higher levels (S. J. Orlow, et al., $J. Invest. Dermatol.$, 94:461–4 (1990)). Indeed, in normal black skin, tyrosinase might be considered to be genetically induced and thus capable of being inhibited by a retinoid, such as retinoic acid (e.g., M. Iwata et al., $J. Invest. Dermatol.$, 95:9–15 (1990)).

This histologic data obtained from biopsies from out patients' skin demonstrated no significant decrease in microscopic epidermal melanin in PIH lesions treated with retinoic acid despite significant clinical lightening. This is surprising because using the same technology as described herein, the same dermatopathologist (LJF) detected significant reduction in epidermal melanin in liver spots which were clinically lightened by RA. (Rafal et al. (1992)).

However, the statistically insignificant decrease in epidermal melanin observed in normal black skin was consistent with the clinical observation of subtle lightening.

Table II shows significant and typical retinoid effects (compaction and increased granular layer) demonstrating pharmacological activity of retinoic acid in the same specimens which exhibited minimal changes in melanin content. It appears that clinically observable differences in skin color can occur in the presence of changes in epidermal melanin content which are essentially undetectable by light microscopy.

A source of potential bias in the present study is the retinoid reaction experienced by some patients. This possibility, although real, is mitigated by the fact that the reaction was seen in only half of the patients treated with retinoic acid. Furthermore, clinical improvement and side effects were graded with reference to pretherapy status throughout the study, without reference to data from previous visits, thus reducing potential bias. Moreover, the calorimeter, an instrument without bias, provided statistically significant corroboration of the lightening observed in both PIH and normal skin upon the administration of the retinolid.

In conclusion, the present study demonstrates that topically applied RA is an effective treatment for black patients with PIH with a side-effect profile similar to or less than that seen in Caucasian skin (Weiss, J. S.; Kligman, A. M.; Weinstein et al., E. S. Rafal et al., C. N. Ellis; and E. A. Olsen, *J. Am. Acad. Dermatol*, 26:215–24 (1992)). Topically applied RA likely is not used presently to treat PIH in black skin due to insufficient experience and reports of unwanted hyperpigmentation, depigmentation and intolerance (McDonald C. J., *Prog. in Dermatol*, 4:15–20 (1973)). The present data demonstrate that normal black skin is not excessively depigmented nor hyperpigmented but is subtly lightened following RA therapy, and that PIH lesions are lightened toward the color of normal black skin.

Other features of the invention will become apparent in the course of the following descriptions of exemplary embodiments which are given for illustration of the invention and are not intended to be limiting thereof.

EXAMPLES

METHODS

Patients:

Sixty-eight, healthy black patients (21 men, 47 women) with moderate to severe PIH lesions on the face and/or arms were enrolled into the 40 week study. The sample size was chosen to provide statistical power of approximately 0.90 in detecting a difference in overall improvement of at least one-half unit between the two groups at a type I error rate of 0.05 using a two-tailed hypothesis. By use of a computer-generated code, subjects were randomly assigned to receive either RA (retinoic acid) or control (vehicle only). Thirty-three subjects received RA (9 men, 24 women) and 35 the control (12 men, 23 women). The age range was 21–58 years, mean 35 years for the RA treatment group and 20–55 years, mean 34 years, for subjects treated with control. Exclusion criteria included medical conditions or concurrent therapy that would interfere with the evaluation 195 of treatment sites. Patients were not to have used topical or systemic retinoids for six months and one year, respectively. Topical medications (including hydroquinone or corticosteroid preparations) or systemic steroids were not used for at least two weeks or for one month, respectively, prior to the study. Pregnant and nursing women, as well as patients with a history of keloids, were excluded from the study.

A pertinent medical history and signed informed consent was obtained from all subjects enrolled. Prior to entering the study, potential side effects were carefully explained to each patient. The protocol was approved by the University of Michigan Medical Center Institutional Review Board.

Treatment:

0.1% retinoic acid cream (commercially available as Retin-AO™ Cream) and control vehicle cream were manufactured and supplied by Ortho Pharmaceutical Corp., Raritan, N.J. Both test creams were packaged and dispensed in identical tubes, such that neither the investigators nor the patients knew the tube contents or to which treatment group the patient was assigned (i.e., a double blind study). Patients applied the test cream once nightly to the entire face and/or arms, depending on the site of PIH lesions, for forty weeks. Patients were initially instructed to apply a pea-sized volume of cream to their skin and to increase gradually the amount of cream applied up to tolerance.

All participants were provided a mild soap or cleansing agent and instructed to wash and then dry the test sites twenty minutes prior to applying the test cream. A sunscreen of SPF 15 was also provided to the participants and they were instructed that it should worn during the day. Patients were instructed to avoid exposure to strong sunlight, excessive wind and cold, and to minimize the use of cosmetics. Cosmetics were not worn during evaluations or photographic sessions. Subjects were warned that erythema (redness), stinging, pruritus, and/or desquamation could result from the treatment and were asked to report these side effects. If side effects were experienced, patients temporarily discontinued treatment for a day or two and used moisturizers supplied by the investigators before continuing therapy.

Evaluations were performed pretherapy, post-therapy at weeks 2 and 4, and then monthly for 10 months. To determine the efficacy of 0.1% RA versus the control vehicle, an overall evaluation of clinical responses of treated areas (face and/or arms) was performed at each return visit and initially graded by the investigator on a scale of 1 to 5 (1=much darker, 5=much lighter) and later regraded according to the following −2 to +2 scale so that a rating of no change would equal zero (−2=much darker; −1=darker; 0=no change; 1=lighter; 2=much lighter).

A separate evaluation of four designated facial and/or upper extremity PIH lesions as well as normal skin was performed on each patient. These four individual PIH lesions were selected as a baseline based on the ability to accurately locate them throughout the investigation. The designated lesions were representative of other lesions in the same patient and were used to correlate pre- and post-therapy clinical and histologic results. At each follow-up visit, changes in pigmentation of designated lesions and changes in color of normal skin on one cheek, as compared with pretreatment, were graded on a scale of 1 to 8 (1=30 much darker, 8=absent) and later reassigned a scale of −3 to +4 (−3=much darker; −2=darker; −1=slightly darker; 0=no change; 1=slightly lighter; 2=lighter; 3=much lighter; and 4=absent) analogous to the method explained above.

Colorimeter:

As an objective measure of skin color of four designated individual PIH lesions and normal skin, a calorimeter (Chroma Meter-CR 200b, Minolta Camera Co. Ltd., Osaka, Japan) was used prior to therapy and at weeks 12, 24, and 40. Colorimetric assessment of skin lightening or darkening is a measure of reflectance which is designated by the L value of the L, a, b color system as defined by the Commission International del'Eclairage (Serup J. et al., *Clinical and*

*Expenimental Dermatology*, 15:267–72 (1990)). Five calorimeter measurements of each site and of normal skin were performed at the above visits and the final measures are given as a mean of these five values.

Safety:

Safety was evaluated as severity of erythema, desquamation, burning/stinging, and pruritus on face or arms and noted at all visits. A scale of 0 to 4 (0=no symptoms and 4=most severe symptoms) was used for these evaluations. Other adverse experiences, new illness, changes in systemic or topical medications, and missed applications of test cream were recorded at each visit.

Light Microscopy:

A 2 mm punch biopsy was taken pre- and post-treatment from a PIH lesion on the face or arm and from normal facial skin. Where feasible a PIH lesion of sufficient size was selected and pre- and post-treatment biopsies were obtained from the same lesion carefully avoiding scar tissue from the pretreatment biopsy. In some patients, due to the small size of the PIH lesions as well as to avoid scar tissue from the pretreatment biopsy, the post-treatment biopsy was taken from a different but nearby PIH lesion.

Specimens were fixed in 10% neutral-buffered formal in, and processed for routine hematoxylin and eosin staining. The histological sections were examined by one dermatopathologist who was not involved in the clinical part of the study and was unaware of the group to which the patient was assigned and which specimens were pre- or post-therapy. The following parameters were evaluated on a scale of zero to four (0=absence and 4=maximum): stratum corneum compaction; granular cell layer thickness; spongiosis; and epidermal and dermal melanin. Epidermal thickness (from the top of the granular layer to the basement membrane zone) in gm was measured in 5 high power fields (HPF). Mitotic figures and melanocyte numbers were counted in 5 HPF and the mean values used.

Statistical Methods:

Changes in clinical and histological parameters of PIH lesions and normal skin from pretherapy to week 40 were compared between RA- and vehicle-treated groups using a two sample t-test. The association between treatment and overall response at week 40 was made with the Chi-Square test. Color changes of PIH lesions in RA- and vehicle-treated groups, assessed by both clinical observation and calorimeter, were compared using the average value of the four designated lesions. In addition, the same comparison was made for normal skin using the designated normal site on the face. In each case, the group means were analyzed using the two-sample t test. The strength of the relation between clinically discernable color change and color change detected by the calorimeter was assessed with Pearson's product-moment correlation coefficient.

All p values are two-sided. Summary statistics are expressed as means ±1 S.E.M. Data were analyzed with the Michigan Interactive Data Analysis System (MIDAS, a statistical software package developed by the Statistical Research Laboratory at the University of Michigan).

Photography:

At the time of the baseline determination and at weeks 12, 24 and 40 of treatment, color photographs for documentation of PIH lesions were taken by a professional photographer. Standardized positioning and broad, diffuse illumination using two studio flash units were used for all patients. A Kodak gray card (18% reflectance) was included in the first frame of each patient's photographic session to control for extrinsic variables. All film was of the same emulsion lot and was processed by the same professional laboratory.

RESULTS:

Of 68 patients enrolled, 14 withdrew prior to completion of the study. Eleven patients withdrew due to noncompliance, not attending scheduled visits (6 in the RA and 5 in the vehicle-treated group), two (both in the RA-treated group) had an exacerbation of eczema and one patient in the RA-treated group experienced a retinoid reaction after two weeks of therapy. The withdrawals were not related to the usage of the experimental cream except in patients who withdrew due to exacerbation of eczema and from retinoid reaction. Therefore, clinical data are presented for 54 subjects (30 in the vehicle-treated group and 24 in the RA-treated group). The major causes of PIH as determined by clinical diagnosis in the subjects enrolled were acne (62 patients), folliculitis (3), eczema (5), ingrown facial hairs (pseudofolliculitis barbae) (4), and shaving irritation (10). Fifteen patients had more than one clinical diagnosis as the cause of PIH.

Figure 1:
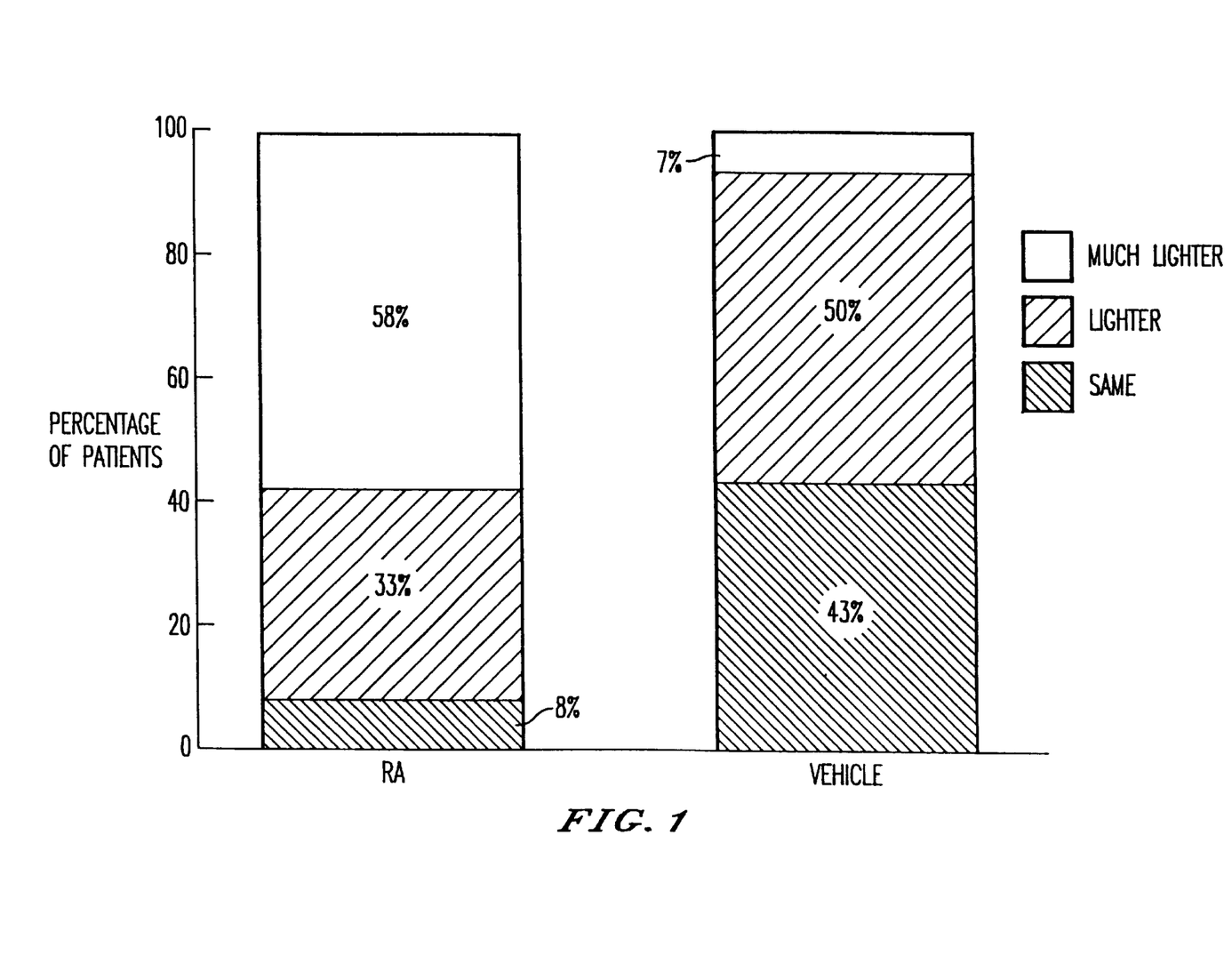
FIG. 1 depicts a comparison of the overall efficacy after 40 weeks of treatment of post-inflammatory hyperpigmentation (PIH) of the face with 0.1% RA (retinoic acid) or a control. As compared with the control, 0.1% RA cream produced significant improvement ($p<0.0001$).
Figure 2:
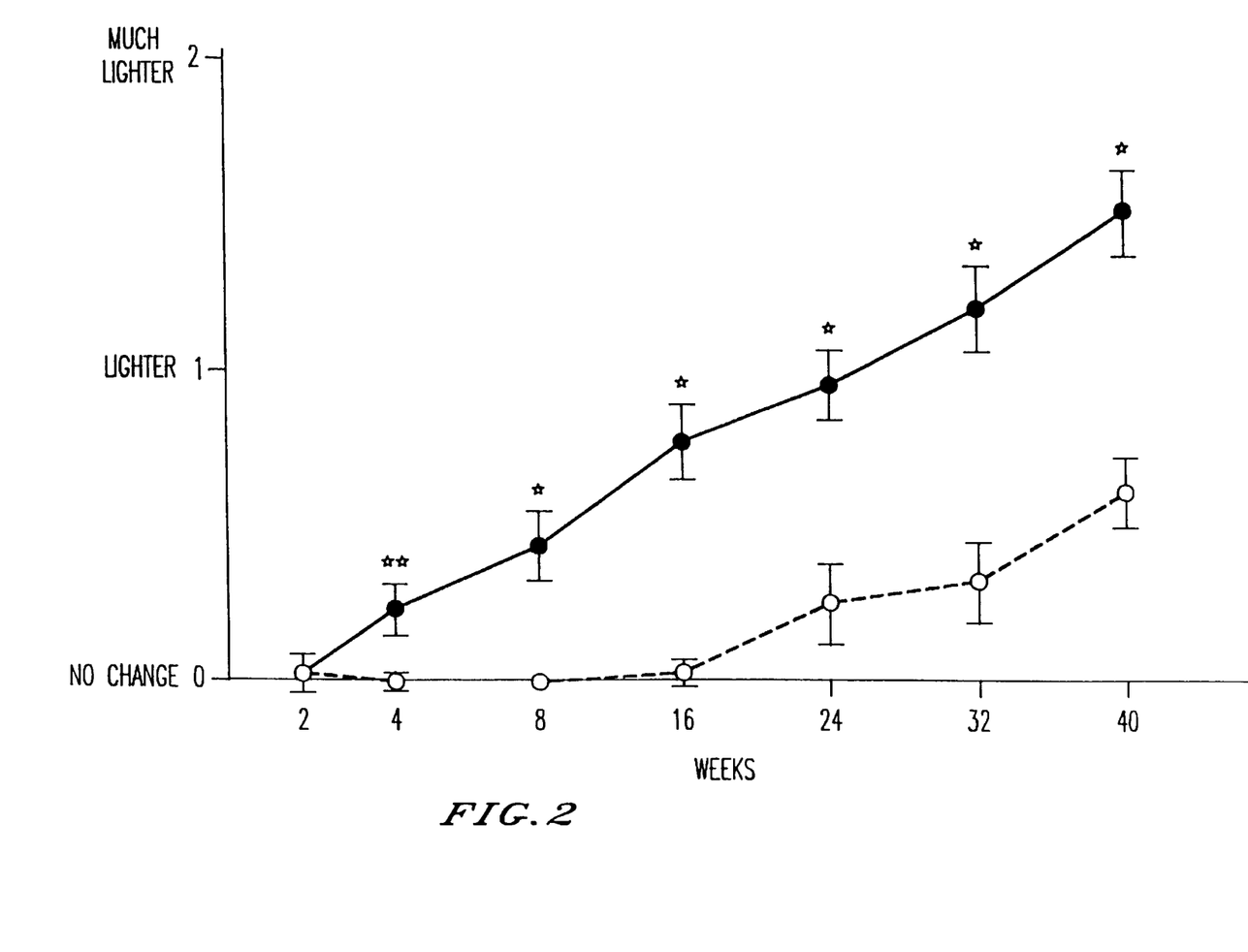
FIG. 2 illustrates the overall color change effected during treatment of facial post-inflammatory hyperpigmentation after treatment with 0.1% RA cream (solid line) or a control composition (broken line). Values shown are means ±SEM. Statistically significant and clinically detectable lightening of lesions was present as early as 4 weeks after initiation of therapy with 0.1% RA ($p=0.009$). This improvement was maintained for all subsequent time points (*, $p \leq 0.0002$). After 16 weeks, the lightening of control-treated lesions is probably due to spontaneous resolution, thereby delineating the natural history of this form of pigmentation.

Overall evaluation of the RA-treated group after 40 weeks, demonstrated clinically significant improvement as compared to the vehicle-treated group (see FIG. 1, p<0.0001). In 14 of 24 (58%) of the RA-treated patients, facial lesions were evaluated as much lighter, in 8 (33%) as lighter and in 2 (8%) the same when compared to pretherapy. In contrast, in vehicle-treated patients, PIH lesions on the face were scored as much lighter in 2 of 30 subjects (7%) of subjects, lighter in 15 of 30 (50%), and unchanged from pretherapy in 13 (43%) (see FIG. 1). Neither group had patients evaluated as worse or much worse. Since only 7 patients had PIH lesions an the arms, overall scores for arms were not included. The time from initiation of RA therapy to when overall lightening of PIH lesions was first achieved was week 4 (see FIG. 2, p=0.009). This clinical improvement was maintained throughout the study when compared to the vehicle group.

Individual PIH lesions: Significant clinical lightening (mean color change from baseline) of RA- versus vehicle-treated PIH lesions was observed after 40 weeks of therapy (2.6±0.2 vs 1.9±0.2, respectively; P=0.03).

Figure 3A:
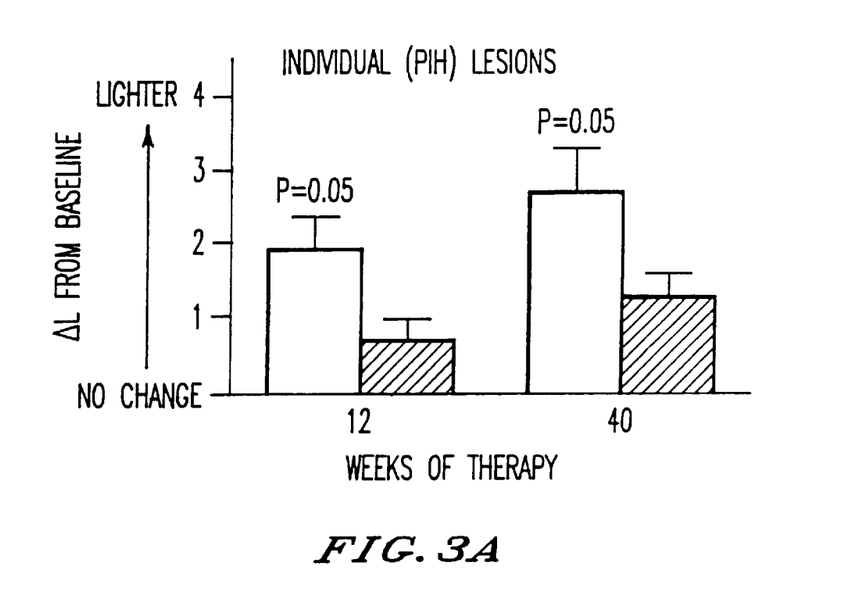
Figure 3B:
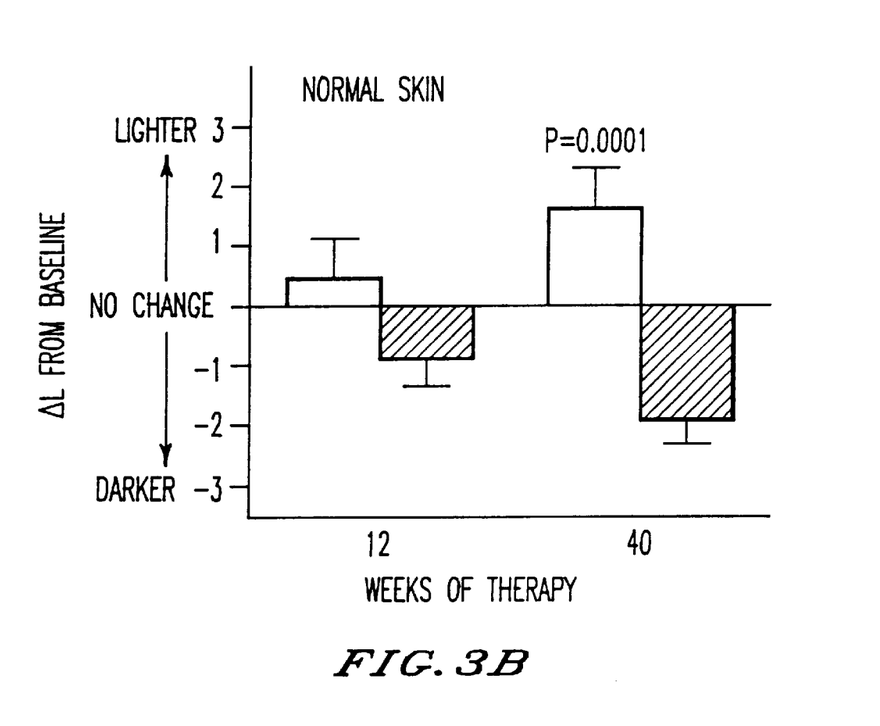

The calorimeter demonstrated an increase in the lightening scale of 2.7±0.7 in PIH lesions treated with RA for 40 weeks compared to an increase of 1.2±0.4 in vehicle-treated lesions (p=0.05, FIG. 3). Since the average pretherapy reflectance (L) value for PIH lesions was 40.6±0.6 and the corresponding average for normal skin was 47.3±0.6, it can be said that 40 weeks of treatment with RA produced a 40 Percent lightening of PIH lesions from their original color toward a normal skin tone compared to an 18% lightening of vehicle-treated lesions. The change in color detected by tie calorimeter from baseline to week 40 was significantly correlated with the clinically discernable color change of the 4 individual PIH lesions (r=0.43, p=0.001)

Normal Skin: The difference in mean color change (clinical lightening) between the RA and vehicle group although statistically significant (p=0.055 using a conservative 2-tailed test) was subtle and barely discernible clinically.

Lightening of RA-treated normal skin was also detected by the calorimeter with an average lightening of 1.6±0.7 compared to a darkening in the vehicle group of 1.9±0.4 (p=0.0001, FIG. 3). Since there is no defined endpoint for lightening of normal skin, it was not possible to quantify the change in terms of percent lightening as done for PIH lesions.

Histology:

Normal skin: Topical RA administration produced statistically significant increases in stratum corneum compaction, granular layer thickness, epidermal thickness, mitotic figures and spongiosis (increased inter-keratinocyte spaces) as compared to vehicle (Table I). After 40 weeks a statistically insignificant (p=0.07) 11% decrease in epidermal melanin was detectable in the RA-treated group in comparison with a 22% increase in the vehicle treated group. In RA-treated patients, a marginally significant (p=0.06) 40% increase in dermal melanin was observed in comparison with a 1% decrease in the vehicle group (Table I).

PIH lesions: Treatment for 40 weeks with topical RA produced statistically significant increases in stratum corneum compaction, granular layer thickness and spongiosis as compared to vehicle (Table II). In RA-treated patients an insignificant (p=0.24f) 28% decrease in epidermal melanin was observed in comparison with a 3% decrease in the vehicle group (Table II). In RA-treated patients an insignificant (p=0.14) 49% increase in dermal melanin was observed in comparison with a 7% decrease in the vehicle group (Table II).

Short Term Safety:

Adverse reactions from use of the RA were limited to a retinoid reaction with minimal to moderate symptoms. A score of 2 or more for erythema or desquamation (on a 0–4 scale where 0=none, 4=severe) at 2 or more visits constituted a retinoid reaction and was observed in 13 of 24 (53%) patients receiving RA and none of vehicle-treated patients. The retinoid reaction was present only in areas that came into contact with active medication. There was a tendency for a gradual diminution in severity, frequency, and duration of reactions as the study progressed. Cutaneous reactions were well tolerated and did not prevent continued participation in the study (apart from 3 subjects). The reactions improved in response to application of emollients or by temporarily reducing or discontinuing the test cream for one to three days. Of note, no subject on RA therapy manifested hyperpigmentation or gross depigmentation as a side effect.

Modifications of and additions to the present invention are possible in light of the above description, which is meant to

TABLE I

NORMAL BLACK SKIN: HISTOLOGY RESULTS
AFTER 40 WEEKS OF TOPICAL RA 0.1% VS. VEHICLE THERAPY

| | RETINOIC ACID (0.1%) n = 24 | | | VEHICLE n = 28 | | | |
|---|---|---|---|---|---|---|---|
| | Pretherapy | Post Therapy | % Change | Pretherapy | Post Therapy | % Change | P value† |
| Epidermal Thickness (μm) | 55 ± 3 | 69 ± 5 | ↑ 26 | 58 ± 3 | 50 ± 2 | ↓ 13 | 0.002 |
| Epidermal Melanin | 1.9 ± 0.2 | 1.6 ± 0.2 | ↓ 11 | 1.6 ± 0.1 | 1.9 ± 0.2 | ↑ 22 | 0.07 |
| Spongiosis | 1.0 ± 0.2 | 1.9 ± 0.2 | ↑ 93 | 1.0 ± 0.2 | 0.7 ± 0.1 | ↓ 27 | 0.001 |
| Granular Cell Layer | 0.8 ± 0.1 | 2.2 ± 0.2 | ↑ 169 | 0.8 ± 0.1 | 0.9 ± 0.1 | ↑ 4 | <0.0001 |
| Stratum Corneum Compaction | 1.3 ± 0.3 | 2.4 ± 0.2 | ↑ 83 | 1.2 ± 0.2 | 1.0 ± 0.2 | ↓ 21 | 0.0003 |
| Dermal Melanin | 1.1 ± 0.2 | 1.5 ± 0.2 | ↑ 40 | 1.4 ± 0.2 | 1.3 ± 0.2 | ↓ 1 | 0.060 |
| Dermal Inflammation | 1.4 ± 0.1 | 1.2 ± 0.2 | ↓ 12 | 1.3 ± 0.1 | 1.2 ± 0.1 | ↓ 7 | 0.74 |
| Melanocyte Number 5/HPF | 25 ± 2 | 27 ± 1 | ↑ 9 | 21 ± 1 | 24 ± 1 | ↑ 18 | 0.48 |
| Mitotic Figures 5/HPF | 0.2 ± 0.1 | 0.5 ± 0.1 | ↑ 225 | 0.5 ± 0.1 | 0.3 ± 0.1 | ↓ 36 | 0.019 |

All measurements represent mean ± SEM and except for epidermal thickness and numbers of mitotic figures and melanocytes are based on a semi-quantitative 0–4 scale where 0 = none and 4 = maximum. Percentages were determined before rounding of the means.
For each patient specimen, measurements from top of granular layer of epidermal basement membrane at 5 inter-rete sites were averaged.
†Represents significance of change from before treatment in the RA versus vehicle groups.

TABLE II

PIH IN BLACK SKIN: HISTOLOGY RESULTS
AFTER 40 WEEKS OF TOPICAL RA 0.1% VS. VEHICLE THERAPY

| | RETINOIC ACID (0.1%) n = 24 | | | VEHICLE n = 28 | | | |
|---|---|---|---|---|---|---|---|
| | Pretherapy | Post Therapy | % Change | Pretherapy | Post Therapy | % Change | P value† |
| Epidermal Thickness (μm) | 76 ± 6 | 82 ± 5 | ↑ 7 | 71 ± 4 | 62 ± 2 | ↓ 13 | 0.077 |
| Epidermal Melanin | 2.2 ± 0.2 | 1.7 ± 0.3 | ↓ 23 | 2.4 ± 0.2 | 2.3 ± 0.2 | ↓ 3 | 0.024 |
| Spongiosis | 1.0 ± 0.2 | 1.9 ± 0.2 | ↑ 84 | 1.2 ± 0.2 | 0.9 ± 0.1 | ↓ 23 | 0.004 |
| Granular Cell Layer | 1.2 ± 0.2 | 2.8 ± 0.2 | ↑ 141 | 1.1 ± 0.2 | 1.5 ± 0.2 | ↑ 39 | 0.001 |
| Stratum Corneum Compaction | 1.7 ± 0.3 | 2.8 ± 0.2 | ↑ 69 | 1.7 ± 0.2 | 1.7 ± 0.2 | ↓ 4 | 0.008 |
| Dermal Melanin | 0.9 ± 0.2 | 1.4 ± 0.2 | ↑ 49 | 1.6 ± 0.2 | 1.5 ± 0.2 | ↓ 7 | 0.140 |
| Dermal Inflammation | 1.6 ± 0.2 | 1.9 ± 0.2 | ↑ 17 | 2.1 ± 0.2 | 1.6 ± 0.2 | ↓ 24 | 0.067 |
| Melanocyte Number 5/HPF | 24 ± 1 | 27 ± 1 | ↑ 13 | 25 ± 1 | 26 ± 1 | ↑ 2 | 0.170 |
| Mitotic Figures 5/HPF | 0.5 ± 0.2 | 0.7 ± 0.2 | ↑ 42 | 0.4 ± 0.1 | 0.3 ± 0.1 | ↓ 30 | 0.230 |

All measurements represent mean ± SEM and except for epidermal thickness and numbers of mitotic figures and melanocytes are based on a semi-quantitative 0–4 scale where 0 = none and 4 = maximum. Percentages were determined before rounding of the means.
For each patient specimen, measurements from top of granular layer of epidermal basement membrane at 5 inter-rete sites were averaged.
†Represents significance of change from before treatment in the RA versus vehicle groups.

be illustrative and not limiting, and so the invention may be practiced otherwise than as specifically described herein yet still within the scope of the appended claims. Such modifications and additions may become apparent to the skilled artisan upon a perusal of this specification, and such are meant to be within the scope and spirit of the invention as defined by the claims.

What is claimed is:

1. A method for treating post-inflammatory hyperpigmentation (PIH) present in black or asian patient's skin, comprising providing a pharmaceutical composition consisting essentially of a dermatologically acceptable retinoid and topically administering to the area of the patient's skin afflicted with PIH a PIH aimeliorating effective nontoxic amount thereof.

2. The method of claim 1, wherein said retinoid is administered in an amount of 0.5 to 10 mg/cm$^2$ of the skin treated.

3. The method of claim 1, wherein said post-inflammatory hyperpigmentation presents in black skin.

4. The method of claim 1, wherein said pharmaceutical composition is in the form of an oil, ointment, cream, lotion, or gel.

5. The method of claim 1, wherein the retinoid is selected from the group consisting of all trns retinoic acid, 9-cis retinoic acid, 13-cis retinoic acid, retinol, and mixtures thereof.

6. The method of claim 1, wherein said pharmaceutical composition further comprises an ingredient selected from the group consisting of water, oils, alcohols, emulsifying agents, odorants, coloring agents, fillers, abrasive agents, moisturizers, and compatible mixtures thereof.

7. The method of claim 1, further comprising administering to said skin an enzyme enhibiting effective amount of a dermatologically acceptable inhibitor of P-450 cytochrome enzyme-mediated degradation of retinoic acid.

8. The method of claim 7, wherein said inhibitor is a triazole.

9. The method of claim 8, wherein the triazole inhibitor is selected from the group consisting of ketoconazole, fluconazole, itraconazole, liarozole, irtemazole, and compatible mixtures thereof.

10. A method of lightening human black skin, comprising providing a pharmaceutical composition consisting essentially of a dermatologically acceptable retinoid in a skin lightening effective amount and topically applying to said human skin an effective thereof.

11. The method of claim 10, wherein said retinoid is administered in an amount of 0.5 to 10 mg/cm$^2$ of the skin treated.

12. The method of claim 10, wherein said pharmaceutical composition is in the form of an oil, ointment, cream, lotion, or gel.

13. The method of claim 10, wherein said pharmaceutical composition further consists essentially of an ingredient selected from the group consisting of water, oils, alcohols, emulsifying agents, perfumes, coloring agents, fillers, abrasive agents, and moisturizers.

14. The method of claim 10, wherein said retinoid is selected from the group consisting of all trns retinoic acid, 9-cis retinoic acid, 13-cis retinoic acid, retinol, and mixtures thereof.

15. The method of claim 10, further comprising administering to said skin an enzyme inhibiting effective amount of a dermatologically acceptable inhibitor of P-450 cytochrome enzyme-mediated degradation of retinoic acid.

16. The method of claim 15, wherein the inhibitor is selected from the group consisting of ketoconazole, fluconazole, itraconazole, liarozole, irtemazole, and compatible mixtures thereof.

17. The method of claim 15, wherein the retinoid is selected from the group consisting of all tmrns retinoic acid, 9-cis retinoic acid, 13-cis retinoic acid, retinol, and mixtures thereof.

18. A method for treating post-inflammatory hyperpigmentation (PIH) in black or asian skin, comprising providing a dermatologically acceptable inhibitor of P-450 cytochrome and applying to the area of said skin afflicted with PIH a PIH aimeliorating effective amount of said inhibitor.

19. The method of claim 18, wherein said inhibitor is an azole.

20. The method of claim 19, wherein the inhibitor is selected from the group consisting of ketoconazole, fluconazole, itraconazole, liarozole, irtemazole, and compatible mixtures thereof.

21. A method for lightening human black skin, comprising providing a dermatologically acceptable inhibitor of P-450 cytochrome enzyme-mediated degradation of retinoic acid and applying to the area of said skin desired to be lightened a skin lightening effective amount of said inhibitor.

22. The method of claim 21, wherein said inhibitor is an azole.

23. The method of claim 21, wherein the inhibitor is selected from the group consisting of ketoconazole, fluconazole, itraconazole, liarozole, irtemazole, and compatible mixtures thereof.

* * * * *